(12) United States Patent
Yamato et al.

(10) Patent No.: US 9,492,135 B2
(45) Date of Patent: Nov. 15, 2016

(54) DYNAMIC RADIOGRAPHIC IMAGING SYSTEM

(71) Applicant: KONICA MINOLTA, INC., Tokyo (JP)

(72) Inventors: Hiroshi Yamato, Amagasaki (JP); Osamu Toyama, Kakogawa (JP); Kenta Shimamura, Takatsuki (JP)

(73) Assignee: KONICA MINOLTA, INC., Tokyo (JP)

(*) Notice: Subject to any disclaimer, the term of this patent is extended or adjusted under 35 U.S.C. 154(b) by 133 days.

(21) Appl. No.: 14/352,041

(22) PCT Filed: Sep. 21, 2012

(86) PCT No.: PCT/JP2012/074159
§ 371 (c)(1),
(2) Date: Apr. 15, 2014

(87) PCT Pub. No.: WO2013/058055
PCT Pub. Date: Apr. 25, 2013

(65) Prior Publication Data
US 2014/0254762 A1    Sep. 11, 2014

(30) Foreign Application Priority Data

Oct. 17, 2011 (JP) .................................. 2011-227990

(51) Int. Cl.
*H05G 1/62* (2006.01)
*A61B 6/00* (2006.01)

(52) U.S. Cl.
CPC .................. *A61B 6/54* (2013.01); *A61B 6/463* (2013.01); *A61B 6/503* (2013.01); *A61B 6/541* (2013.01); *A61B 6/542* (2013.01)

(58) Field of Classification Search
CPC ........ A61B 6/54; A61B 6/541; A61B 6/503; A61B 6/542; H05G 1/62
USPC ....................................... 378/8, 95
See application file for complete search history.

(56) References Cited

U.S. PATENT DOCUMENTS

| 5,482,042 A | 1/1996 | Fujita |
| 6,633,775 B1 * | 10/2003 | Bernard ................. A61B 6/541 378/95 |

(Continued)

FOREIGN PATENT DOCUMENTS

| JP | 07-023945 | 1/1995 |
| JP | 3793102 B2 | 9/2003 |

(Continued)

OTHER PUBLICATIONS

Office Action in Japanese Patent Application No. 2013-539581 dated Aug. 18, 2015, and English language translation, 6 pages.
International Search Report in International Application No. PCT/JP2012/074159 mailed Oct. 23, 2012, 2 pages.

(Continued)

*Primary Examiner* — Jurie Yun
(74) *Attorney, Agent, or Firm* — Brinks Gilson & Lione

(57) ABSTRACT

A dynamic radiographic imaging system includes a detecting section that detects periodic changes of a predetermined site of a subject; a recommended imaging (start) timing specifying section that specifies a recommended imaging start timing based on the detection result; a notifying section that makes a notification to a photographer in multiple stages as the recommended imaging start timing approaches; an operation unit that receives an instruction input from the photographer to start radiation imaging of the subject; and an image capturing control section that controls the radiation imaging in response to the instruction input by the operation unit. The dynamic radiographic imaging thus can be performed at an appropriate imaging timing without depending on the level of skill of the photographer for the body site that periodically changes such as the heart.

2 Claims, 12 Drawing Sheets

(56) References Cited

U.S. PATENT DOCUMENTS

| | | | |
|---|---|---|---|
| 6,689,059 B2 * | 2/2004 | Harder | A61B 5/044 600/300 |
| 7,492,936 B2 | 2/2009 | Inoue | |
| 2009/0175416 A1 | 7/2009 | Yamanaka | |

FOREIGN PATENT DOCUMENTS

| | | |
|---|---|---|
| JP | 2004-57559 A | 2/2004 |
| JP | 2005-270286 | 10/2005 |
| JP | 2005-312776 | 11/2005 |
| JP | 2006-158762 A | 6/2006 |
| JP | 2008-228914 | 10/2008 |
| WO | WO 2007/046220 A1 | 4/2007 |

OTHER PUBLICATIONS

"Unrestrained Respiration Monitoring for Sleeping Person Using Fiber Grating Vision Sensor," Aoki, Hirooki, and Nakajima, Masato, Dept. of E.E. Fac. of Sci. and Tec., Keio Univ., Institute of Electronics, Information, and Communication Engineers conference lecture paper collection, 2001, Information and System Society Conference Lecture paper Collection, pp. 320-321, dated Aug. 29, 2001, 5 pages, including English language translation.

* cited by examiner

F I G . 3
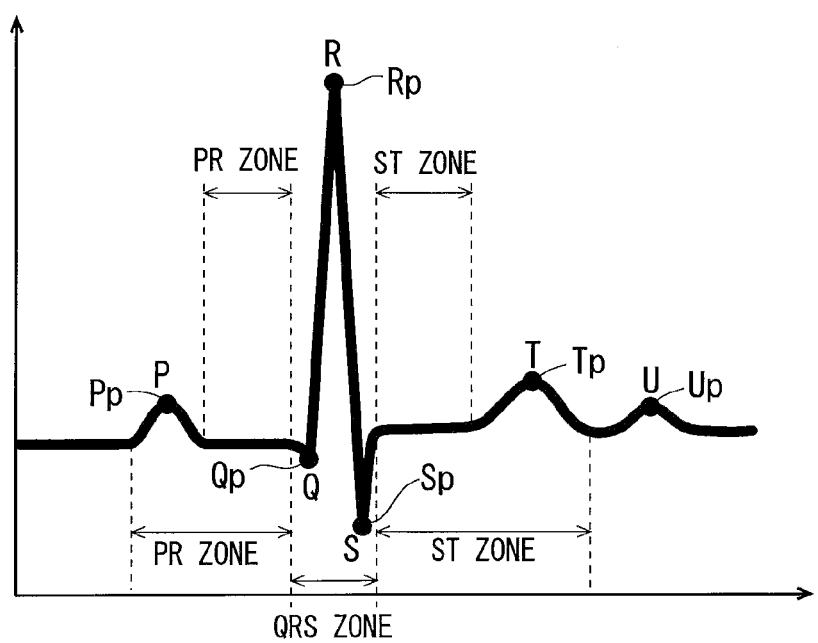
F I G . 4
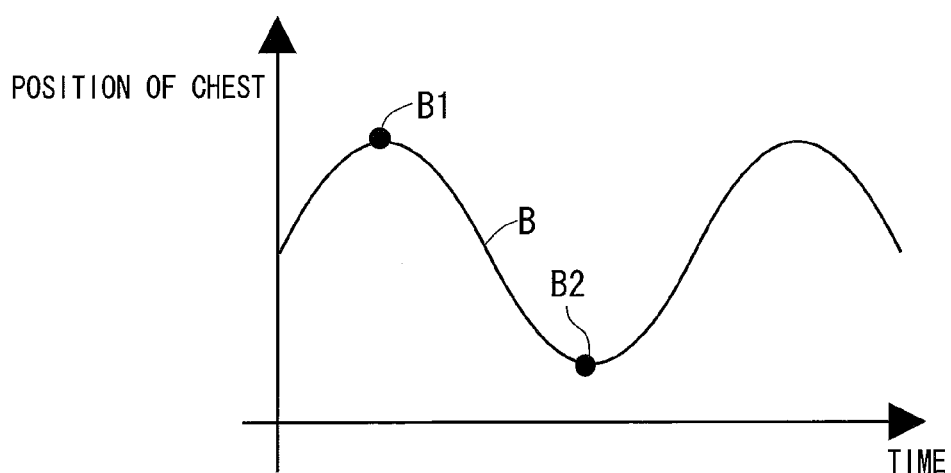

DYNAMIC RADIOGRAPHIC IMAGING SYSTEM

This application is a National Stage application of International Application No. PCT/JP2012/074159, filed Sep. 21, 2012.

TECHNICAL FIELD

The present invention relates to a dynamic radiographic imaging technique for imaging a human body or a body of an animal using radiation.

BACKGROUND ART

In medical practice, various tests and diagnoses are carried out by imaging an affected area included in an internal organ, skeleton, and the like using X-rays and the like. In recent years, a dynamic image in which the movement of the affected area is captured can be acquired relatively easily using the X-ray and the like due to the application of digital technique.

Since the dynamic image can be imaged with respect to a subject region including a target site using a semiconductor image sensor such as an FPD (Flat Panel Detector), diagnosis by movement analysis of the target site and the like, which cannot be performed in the still imaging and diagnosis by the conventional X-ray imaging, can be performed. For example, consideration for assisting (X-ray dynamic image CAD) the diagnosis/treatment is also being performed by extracting the ventilation information in the lung field from the chest X-ray dynamic image, and performing the quantitative analysis of the dynamic function from the change and movement in concentration in the lung field, and the like.

The determining method of the imaging start/end timing in performing the diagnosis includes an automatic imaging start/end timing determining method and a manual imaging start/end timing determination method.

As for the automatic imaging start/end timing determining method, there is Patent Document 1, for example. In the technique disclosed in Patent Document 1, a respiration cycle is detected by another device, and an imaging timing including at least one of an imaging start timing and an imaging end timing is automatically controlled according to the respiration cycle.

On the other hand, in the manual imaging start/end timing determining method, the desired timing is determined by the operation of the photographer.

In addition, Patent Document 2 discloses a technique of performing the imaging at low irradiation amount in a predetermined frame rate, detecting a change amount of an image between the frames, and setting a frame rate of the imaging at high irradiation amount based on the change amount.

PRIOR ART DOCUMENT

Patent Document

Patent Document 1: Japanese Patent No. 3793102
Patent Document 2: Japanese Patent Application Laid-Open No. 2008-228914

SUMMARY OF INVENTION

Problems to be Solved by the Invention

However, in the technique of Patent Document 1, the imaging is automatically started according to the detection of the respiration cycle, and hence the start of the imaging cannot be canceled even when unexpected disturbance of breathing and the like occurred and wasteful imaging might be carried out.

On the other hand, in the manual imaging start/end timing determining method, the imaging at the desired timing can be carried out while checking the state of the subject, but this is strongly influenced by the experience of the photographer. In other words, the photographer of less experience may not know the imaging start/end timing well and hence there is a possibility the imaging of a necessary period cannot be performed.

In the technique of Patent Document 2, the frame rate of the imaging at high irradiation amount is set by the change amount of the image, but at what timing to start the serial imaging at high irradiation amount is not suggested.

The present invention has been made in light of the foregoing, and an object thereof is to provide a dynamic radiographic imaging technique for starting the imaging at an appropriate timing without depending on the level of skill of the photographer when obtaining the dynamic radiographic image of the subject, the subject being the human body or the body of the animal.

Means for Solving the Problems

A dynamic radiographic imaging system according to a first aspect of the present invention relates to a dynamic radiographic imaging system that performs imaging of a radiation image of a subject, the subject being a human body or a body of an animal, the dynamic radiographic imaging system including a detecting section that detects periodic changes of a predetermined site of the subject, a recommended imaging start timing specifying section that specifies a recommended imaging start timing based on the detection result of the detecting section, a notifying section that makes a notification to an photographer in multiple stages as the recommended imaging start timing approaches, an operation unit that receives an instruction input from the photographer to start the radiation imaging of the subject, and an imaging control unit that starts the radiation imaging of the subject in response to the instruction input by the operation unit.

Effects of the Invention

According to the present invention, the photographer can easily grasp the appropriate imaging start timing and can start the imaging at an arbitrary timing while observing the subject by making the notification to the photographer in multiple stages as the recommended imaging start timing approaches. Thus, the imaging can be started at an appropriate timing without depending on the level of skill of the photographer, and wasteful imaging can be prevented from being carried out.

BRIEF DESCRIPTION OF DRAWINGS

FIG. 3 is a schematic view showing a part of a waveform measured with an electrocardiographic monitor.

FIG. 4 is a view illustrating a temporal change in the detection information of a cycle detection device 16.

DESCRIPTION OF EMBODIMENTS

<1. First Embodiment>

A dynamic radiographic imaging system according to a first embodiment of the present invention will be hereinafter described.

<1-1. Overall Configuration of Dynamic Radiographic Imaging System>

The dynamic radiographic imaging system according to the first embodiment performs the imaging of a radiation image of a subject, the subject being a human body or a body of an animal.

Figure 1:
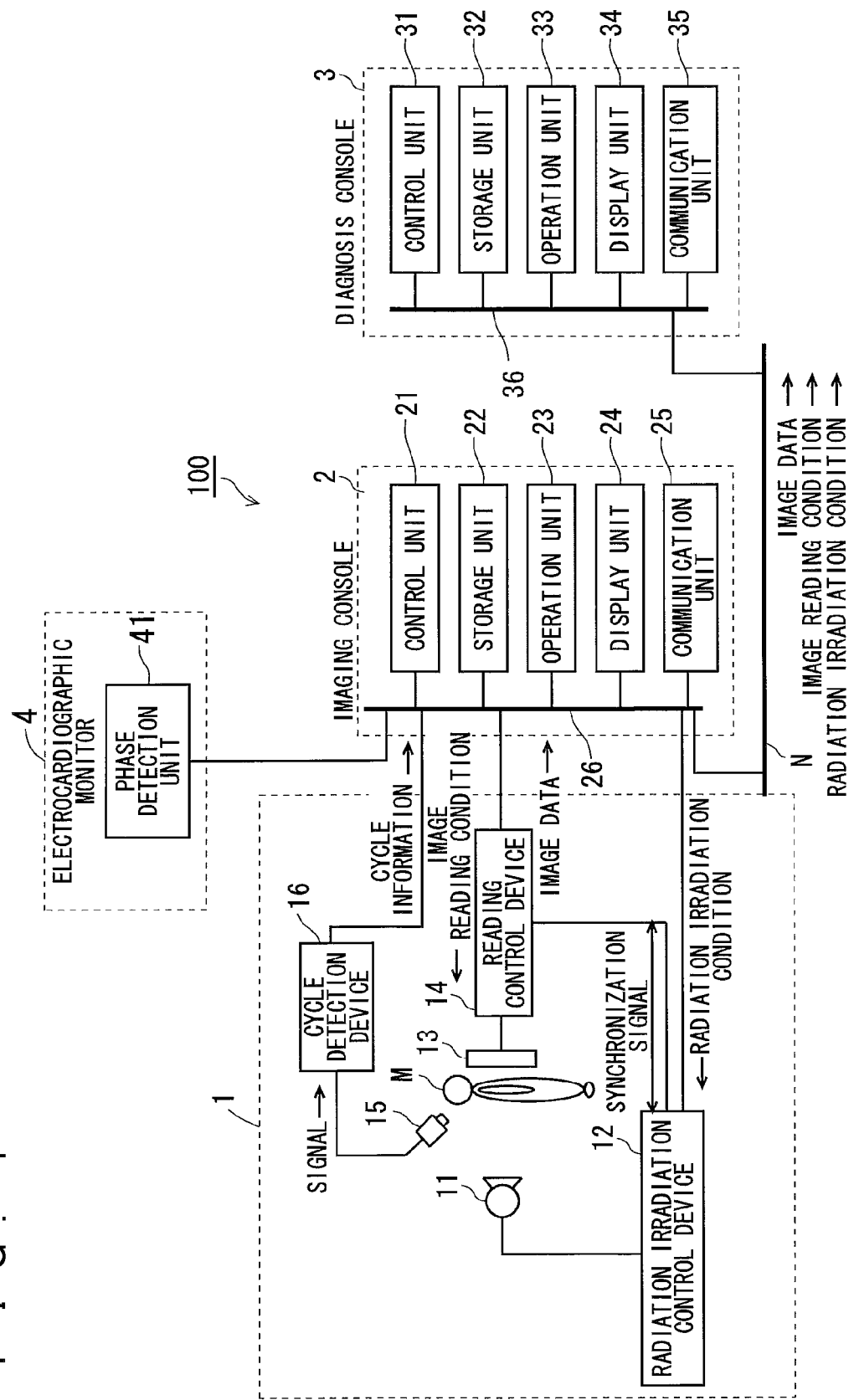
FIG. 1 is a view showing an overall configuration of a dynamic radiographic imaging system 100 according to a first embodiment.

FIG. 1 is a view showing an overall configuration of the dynamic radiographic imaging system according to the first embodiment. As shown in FIG. 1, a dynamic radiographic imaging system 100 includes an imaging device 1, an imaging console 2, a diagnosis console 3, and an electrocardiographic monitor 4. In this configuration, the imaging device 1 and the electrocardiographic monitor 4 are connected to the imaging console 2 through a communication cable and the like, and the imaging console 2 is connected to the diagnosis console 3 through a communication network NT such as LAN (Local Area Network). Each of the devices configuring the dynamic radiographic imaging system 100 complies with a DICOM (Digital Image and Communications in Medicine) standard, and the communication between the devices is carried out in accordance with the DICOM standard.

<1-1-1. Configuration of Imaging Device 1>

The imaging device 1 is a device configured, for example, by an X-ray imaging device and the like, and for imaging a dynamic state of the chest of a subject M involved in breathing. The imaging of the dynamic state is carried out by acquiring a plurality of images in time sequential manner while repeatedly irradiating the chest of the subject M with radiation such as X-rays. A series of images obtained by such serial imaging is referred to as dynamic images. Each of the plurality of images configuring the dynamic image is referred to as a frame image.

As shown in FIG. 1, the imaging device 1 is configured to include an irradiation unit (radiation source) 11, a radiation irradiation control device 12, an image capturing unit (radiation detecting section) 13, a reading control device 14, a cycle detection sensor 15, and a cycle detection device 16.

The irradiation unit 11 irradiates the subject M with radiation (X-rays) according to the control of the radiation irradiation control device 12. The illustrated example is a system for human body, and the subject M corresponds to the test target. Hereinafter, the subject M is also referred to as "test subject".

The radiation irradiation control device 12 is connected to the imaging console 2, and controls the irradiation unit 11 based on the radiation irradiation conditions input from the imaging console 2 to perform radiation imaging.

The radiation irradiation conditions input from the imaging console 2 are, for example, a pulse rate, a pulse width, a pulse interval, a value of X-ray tube current, a value of X-ray tube voltage, a filter type, and the like at the time of successive irradiation. The pulse width is the radiation irradiation time per one radiation irradiation, and the pulse interval is the time from the start of one radiation irradiation to the start of the next radiation irradiation in the serial imaging.

The image capturing unit 13 is configured by a semiconductor image sensor such as an FPD, and converts the radiation, which is emitted from the irradiation unit 11 and transmitted through the test subject M, to an electric signal (image information). The FPD includes a glass substrate and the like, for example, where a plurality of unit elements that receive the radiation emitted from the irradiation unit 11 and transmitted through at least the test subject M, accumulate the charges according to the intensity of the radiation, and output the electric signal corresponding to the accumulated amount of charges are arrayed in a matrix form at a predetermined position on the substrate. Each unit element corresponds to a pixel, and for example, is configured by a switching unit such as a TFT (Thin Film Transistor).

The reading control device 14 is connected to the imaging console 2. The reading control device 14 controls the switching unit of each pixel of the image capturing unit 13 based on the image reading conditions input from the imaging console 2 to switch the reading of the electric signal accumulated in each pixel and read the electric signal accumulated in the image capturing unit 13, thus acquiring the image data. The reading control device 14 outputs the acquired image data (frame image) to the imaging console 2. The image reading conditions are, for example, a frame rate, a frame interval, a pixel size, a image size (matrix size), and the like. The frame rate is the number of frame images acquired per one second, and coincides with the pulse rate. The frame interval is the time from the start of the acquiring operation of the frame image of one time to the start of the acquiring operation of the frame image of next time in the serial imaging, and coincides with the pulse interval.

The radiation irradiation control device 12 and the reading control device 14 are connected to each other and exchange synchronization signals with each other to tune the radiation irradiation operation and the operation of reading the image.

The cycle detection device 16 detects the respiration cycle of the subject M and outputs the cycle information to a control unit 21 of the imaging console 2. The cycle detection device 16 includes, for example, the cycle detection sensor 15 for detecting the movement of the chest of the subject M (respiration cycle of the subject M) by laser irradiation, and a timing unit (not shown) for measuring the time of the respiration cycle detected by the cycle detection sensor 15 and outputting the measured time to the control unit 21.

<1-1-2. Configuration of Imaging Console 2>

The imaging console 2 outputs the radiation irradiation conditions and the image reading conditions to the imaging device 1 to control the radiation imaging and the reading operation of the radiation image by the imaging device 1, and also displays the dynamic image acquired by the imaging device 1 to check positioning by the imaging technician and to check whether or not the image suited for diagnosis.

As shown in FIG. 1, the imaging console 2 is configured to include the control unit 21, a storage unit 22, an operation unit 23, a display unit 24, and a communication unit 25, and the units are connected by a bus 26.

The control unit 21 is configured by a CPU (Central Processing Unit), a RAM (Random Access Memory), and the like. The CPU of the control unit 21 reads out system programs and various types of processing programs stored in the storage unit 22 and develops the same in the RAM according to the operation of the operation unit 23, executes various types of processing including the imaging control process, to be described later, according to the developed program, and intensively controls (details will be described later) the operation of each unit of the imaging console 2 and the operation of the imaging device 1. A timer (not shown) is also connected to the control unit 21.

The storage unit 22 is configured by a nonvolatile semiconductor memory, a hard disk, and the like. The storage unit 22 stores various types of programs to be executed by the control unit 21 and parameters necessary for the execution of the process by the program, or data such as the processing result.

For example, the storage unit 22 stores the imaging control processing program for executing the imaging control process, to be described later. The storage unit 22 also stores the radiation irradiation conditions and the image reading conditions. The various types of programs are stored in a form of readable program codes, and the control unit 21 sequentially executes the operations according to the relevant program code.

The storage unit 22 also stores a respiration cycle table. The respiration cycle table is a table that stores a range of reference time (second) of one respiration cycle when the breathing is stable for each category (toddler, child, adult (male), . . . ) of the test subject M. The category of the test subject M is sectionalized according to the test subject information (age, sex).

The operation unit 23 is configured to include a keyboard with a cursor key, number input keys, various function keys, and the like, and a pointing device such as a mouse, and outputs an instruction signal, which is input by the key operation on the keyboard or the mouse operation, to the control unit 21. The operation unit 23 may include a touch panel on a display screen of the display unit 24, in which case, the operation unit 23 outputs an instruction signal input through the touch panel to the control unit 21.

The display unit 24 is configured by a monitor such as a color LCD (Liquid Crystal Display), and displays the input instruction, data, and the like from the operation unit 23 according to the instruction of the display signal input from the control unit 21.

The communication unit 25 includes a LAN adapter, a modem, a TA (Terminal Adapter), and the like, and controls data transmission/reception with each device connected to the communication network NT.

<1-1-3. Configuration of Diagnosis Console 3>

The diagnosis console 3 is a device for displaying the dynamic image transmitted from the imaging console 2 so that the doctor can interpret the radiogram and make a diagnosis.

As shown in FIG. 1, the diagnosis console 3 is configured to include a control unit 31, a storage unit 32, an operation unit 33, a display unit 34, and a communication unit 35, and the units are connected by a bus 36.

The control unit 31 is configured by a CPU, a RAM, and the like. The CPU of the control unit 31 reads out system programs and various types of processing programs stored in the storage unit 32 and develops the same in the RAM according to the operation of the operation unit 33, executes various types of processing according to the developed program, and intensively controls the operation of each unit of the diagnosis console 3.

The storage unit 32 is configured by a nonvolatile semiconductor memory, a hard disk, and the like. The storage unit 32 stores various types of programs to be executed by the control unit 31 and parameters necessary for the execution of the process by the program, or data such as the processing result. The various types of programs are stored in a form of readable program codes, and the control unit 31 sequentially executes the operation according to the relevant program code.

The operation unit 33 is configured to include a keyboard with a cursor key, number input keys, various function keys, and the like, and a pointing device such as a mouse, and outputs an instruction signal, which is input by the key operation on the keyboard or the mouse operation, to the control unit 31. The operation unit 33 may include a touch panel on a display screen of the display unit 34, in which case, the operation unit 33 outputs an instruction signal input through the touch panel to the control unit 31.

The display unit 34 is configured by a monitor such as a color LCD, and displays the input instruction, data, and the like from the operation unit 33 according to the instruction of the display signal input from the control unit 31.

The communication unit 35 includes a LAN adapter, a modem, a TA, and the like, and controls data transmission/reception with each device connected to the communication network NT.

<1-1-4. Configuration of Electrocardiographic Monitor 4>

In FIG. 1, the electrocardiographic monitor 4 is shown distant from the test subject M, but actually, each electrode terminal of the electrocardiographic monitor 4 is attached to the test subject M and outputs an electrocardiographic waveform of the test subject M as a digital signal.

As shown in FIG. 1, the electrocardiographic monitor 4 is configured to include a phase detecting section 41, the phase detecting section 41 detecting a phase of a heartbeat of the subject M as basic information for synchronizing the imaging operation by the imaging device 1 in response to a control signal from the CPU of the control unit 21. The phase detecting section 41 may also be arranged in the imaging console 2.

<1-2. Specific Configuration of Dynamic Radiographic Imaging System 100>

In the dynamic radiographic imaging system 100 according to the first embodiment of the present invention, the recommended imaging timing is specified based on the detection result of the periodic changes in the heart (first site) of the test subject M, notification of such is made to the photographer in multiple stages as the recommended imaging timing approaches, and the imaging is started in response to the instruction input from the photographer.

Generally, the timing to make a notification to the photographer may be the "recommended imaging timing" that includes both "recommended imaging start timing" and "recommended imaging end timing", but among them, the "recommended imaging start timing" is particularly important and will be centrally described below.

Specifically, a specific phase in the periodic changes (heartbeat) of the heart of the test subject M is determined as the recommended imaging start timing, and the doctor (or radiology technician), who is the photographer, is notified of this in multiple stages as the recommended imaging timing approaches. Furthermore, the system 100 mainly assumes the chest of the test subject M as the imaging target, where the imaging target includes the lung (another site) as a site that periodically time changes in a time period different from the heart (predetermined site).

A mode in which the recommended imaging timing is determined based on the phase of the heartbeat will be mainly described below, but the recommended imaging timing may be determined based on the phase in the lung respiration or in this regards, the correspondence relationship of the "target (predetermined) site" and the "another site" may be reversed.

A functional configuration realized by the imaging console 2 will be described below.

<1-2-1. Function Configuration of Dynamic Radiographic Imaging System 100>

Figure 2:
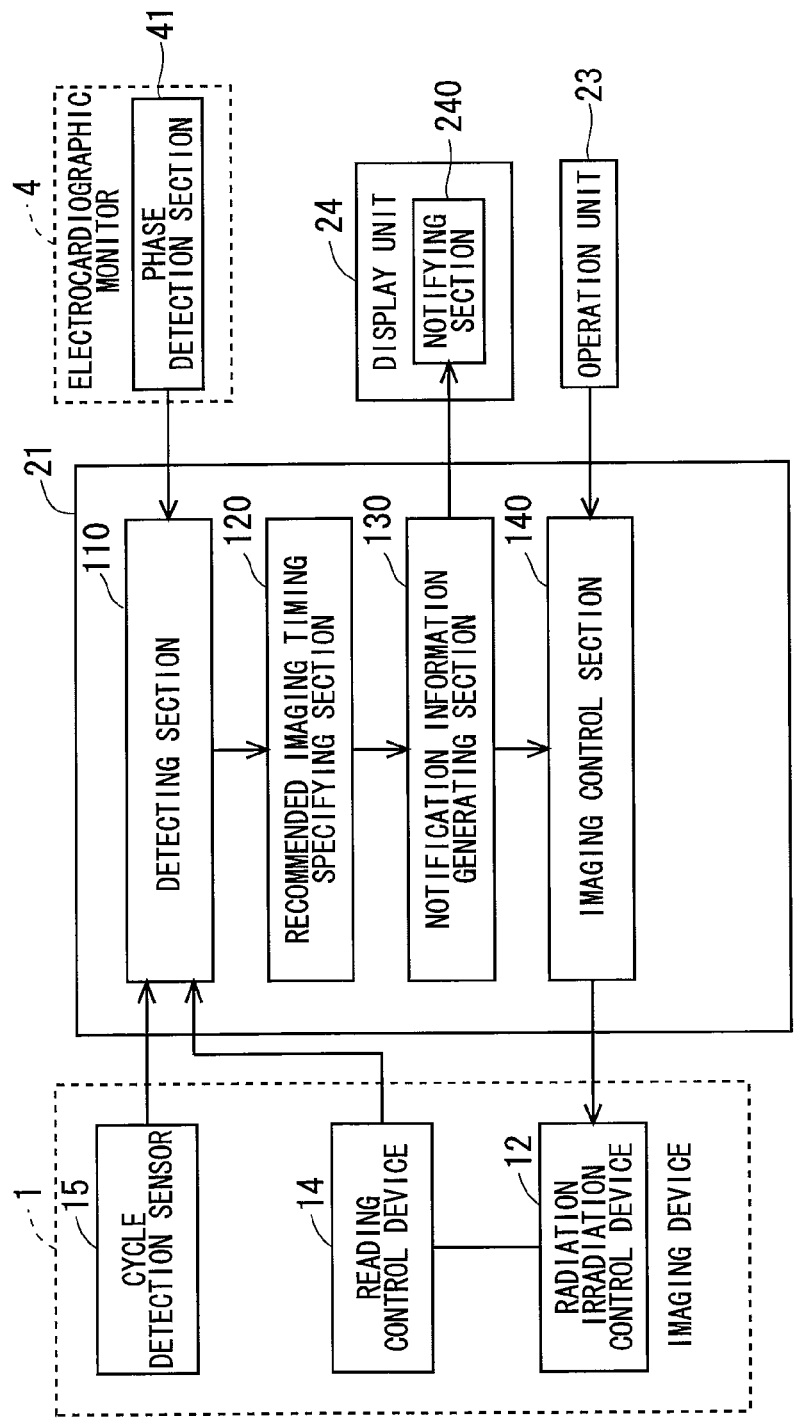
FIG. 2 shows a block diagram showing a function configuration of the dynamic radiographic imaging system 100 according to the first embodiment.

FIG. 2 is a view showing, along with other configurations, the function configuration realized by the control unit 21 and the function configuration realized by the display unit 24 when the CPU and the like operate according to various types of programs in the imaging console 2 of the dynamic radiographic imaging system 100. The dynamic radiographic imaging system 100 of the present embodiment is mainly used to image the dynamic image of the chest including the heart and both lungs.

The control unit 21 includes a detecting section 110, a recommended imaging timing specifying section 120, a notification information generating section 130, and an image capturing control section 140.

The display unit 24 includes a color display for visual display and a sound source for auditory display (auditory notification information), and also includes a notifying section 240 for performing a notification control as will be described later.

Hereinafter, the functional configuration of the control unit 21 shown in FIG. 2 will be described as being realized by the execution of the program installed in advance, but may be realized by dedicated hardware configuration.

The specific content for each process performed by the detecting section 110, the recommended imaging timing specifying section 120, the notification information generating section 130, the notifying section 240, and the image capturing control section 140 will be hereinafter sequentially described while referencing FIG. 2.

<1-2-1-1. Detecting Section 110>

In the detecting section 110, the periodic changes of the heart and the lung of the test subject M, that is, the phase information and the frequency (periodic) information of the heartbeat and the breathing are detected. The detection of time change in this case means the detection of the temporal change on the geometric state such as the outer shape of the organ.

In other words, the detecting section 110 is configured to include a detecting section that detects the periodic changes of the target site of the subject M and a second detecting section that detects the periodic changes of another site different from the target site of the subject M.

A calculation method for the periodic information by heartbeat and the periodic information by breathing will be hereinafter described.

<1-2-1-1-1. Heartbeat Information Detection Method: Detection Result of Electrocardiographic Monitor>

The heartbeat information detection method includes a method that uses the result acquired from the phase detecting section 41 of the electrocardiographic monitor 4. FIG. 3 is a view illustrating an electrocardiographic waveform of the test subject M. In FIG. 3, the horizontal axis indicates time and the vertical axis indicates magnitude (voltage) of the electric signal, and curves showing the change in electric signal including curves Pp, Qp, Rp, Sp, Tp, and Up, each showing the shape of the so-called P wave, Q wave, R wave, S wave, T wave, and U wave are shown.

In the detecting section 110, the points (Pp, Qp, Rp, Sp, Tp, and Up), the interval (PR, QRS, and ST), and the zone (PR and ST) are detected based on the detection result acquired from the phase detecting section 41.

<1-2-1-1-2. Breathing Information Detection Method: Measurement Result by Another Device>

The breathing information detection method is performed with measurement by another device. A device described in Japanese Patent No. 3793102, for example, may be used for the method for measurement by another device. There may be adopted a method for performing by monitoring with a sensor configured by laser light and a CCD camera (see e.g., "Unrestrained Respiration Monitoring for Sleeping Person Using Fiber Grating Vision Sensor" by Hirooki AOKI, Masato NAKAJIMA, Institute of Electronics, Information, and Communication Engineers conference lecture paper collection, 2001, Information and system society conference lecture paper collection, 320-321, 2001-08-29 etc.), for example.

In the present embodiment, the cycle detection sensor 15 of the cycle detection device 16 can be used. Another method for detecting the respiration cycle includes a method for detecting the movement of the chest of the subject using the respiration monitor belt and a method for detecting the air flow of breathing by an air velocity meter, which methods can also be applied.

FIG. 4 is a view showing the temporal change in the detection information of the cycle detection device 16 with the horizontal axis indicating the time direction and the vertical axis indicating the position of the chest. In other words, the result of detecting the movement of the chest with the breathing information detection method described above, and monitoring the same in the time direction is shown.

As shown in FIG. 4, the period of breathing (respiration cycle) B can be acquired by acquiring the position of the chest in the time direction. One period of the respiration cycle B is configured by inhalation and exhalation, and includes one exhalation and one inhalation. In inhalation, the region of the lung field in the rib cage becomes larger as the diaphragm lowers and air is drawn in. The time (conversion point of inhalation and exhalation) when the air is drawn in to a maximum extent is a maximum inhalation time B1. In exhalation, the region of the lung field becomes smaller as the diaphragm rises and the air is exhaled, where the time (conversion point of exhalation and inhalation) when the air is exhaled to a maximum extent is a maximum exhalation time B2.

An area where the change amount of the respiration cycle B changes from positive to negative is hereinafter referred to as the "maximum change state", and an area where the change amount changes from negative to positive is referred to as the "minimum change state". In the case of FIG. 4, the maximum change state of the position of the chest represents the maximum inhalation time B1, and the minimum change state of the position of the chest represents the maximum exhalation time B2.

<1-2-1-2. Recommended Imaging Timing Specifying Section 120>

In the recommended imaging timing specifying section 120 of FIG. 2, the recommended imaging timing is specified based on the detection result of the detecting section 110. The recommended imaging timing is information for specifying a specific time point in the future, and includes at least the recommended imaging start timing.

In other words, the recommended imaging timing specifying section 120 is configured to include a recommended imaging start timing specifying section that specifies the recommended imaging start timing based on the detection result of the detecting section 110, and a recommended imaging end timing specifying section that specifies the recommended imaging end timing based on the detection result of the detecting section 110.

As described above, the imaging target includes the target site and another site that respectively time changes at a unique period, and the recommended imaging timing specifying section 120 specifies the recommended imaging start timing in correspondence with the specific phase of the periodic changes of the target site (heart) (hereinafter referred to as "simple phase control"). In the simple phase control, the imaging of another site (lung) is guaranteed to be performed at the timing corresponding to the specific phase of the target site, and is less likely to be subjected to the influence of the difference in the phase of the target site.

This also applies to an opposite relationship where the target site is the lung and another site is the heart.

Furthermore, the recommended imaging timing specifying section 120 may specify the timing at which a first specific phase in the periodic changes of the target site and a second specific phase in the periodic changes of another site overlap as the recommended imaging start timing (hereinafter referred to as "two-way phase control"). In the two-way phase control, the recommended imaging start timing is defined as the timing at which the first specific phase of the target site and the second specific phase of another site overlap, and thus imaging in a state where each of the two types of sites is the at desired phase can be carried out.

When defining the recommended imaging start timing in the relationship with the site that periodically changes as described above, the recommended imaging start timing may be defined not as a point on the time having a time width of zero but as a timing having a very short (not zero) time width compared to the period (heartbeat period etc.) to become the basis of timing determination. The recommended imaging end timing is also similarly defined.

The specifying method of the recommended imaging start timing and the specifying method of the recommended imaging end timing will be sequentially described below.

<1-2-1-2-1. First Recommended Imaging Start Timing Specifying Method: Heartbeat Information>

The first recommended imaging start timing specifying method corresponds to the simple phase control, and uses the heartbeat information detected with the heartbeat information detection method described above by the detecting section 110. In other words, the recommended imaging start timing is specified with the signal generation time that can be captured with the electrocardiographic monitor 4 as the base. For example, with the position of point Pp as the specific phase in the electrocardiographic waveform of FIG. 3, the generation recommended imaging start timing may be specified by the time corresponding thereto, or with the position of point Rp as the specific phase, the recommended imaging start timing may be specified by the time corresponding thereto.

<1-2-1-2-2. Second Recommended Imaging Start Timing Specifying Method: Breathing Information>

The second recommended imaging start timing specifying method corresponds to the simple phase control, and uses the breathing information detected with the breathing information detection method described above by the detecting section 110. In other words, the recommended imaging start timing may be specified with the maximum inhalation time B1 in the respiration cycle B acquired by the cycle detection sensor 15 or another device as the specific phase, or the recommended imaging start timing may be specified with the maximum exhalation time B2 as the specific phase (see FIG. 4).

However, if the phase detection of the respiration is not carried out in another device such as the cycle detection sensor 15 and the respiratory phase is specified based on each frame image of the dynamic X ray image imaged in the past, the timing at which the specific phase of the respiration arrives next is estimated based on prediction calculation. This is because the acquisition of the X-ray frame image is intermittently carried out and the X-ray irradiation is not performed at the time point that the acquisition of the previous X-ray frame image is completed and the imaging for the next X-ray frame image needs to be started, and thus the image indicating the state of the test subject M at the current time point cannot be referenced and the X-ray frame image at the past time point is merely acquired. Therefore, for example, the recommended imaging start timing corresponding to the specific phase of the respiration is specified by extrapolating temporally in a future direction the temporal change information of the phase obtained from the X-ray frame images obtained by the previous imaging.

<1-2-1-2-3. Third Recommended Imaging Start Timing Specifying Method: Heartbeat and Breathing Information>

The third recommended imaging start timing specifying method corresponds to the two-way phase control, and uses the heartbeat information detected with the heartbeat information detection method and the breathing information detected with the breathing information detection method by the detecting section 110. In other words, the time point at which the first and second recommended imaging start timing specified from the respective phases of the heartbeat and the breathing coincide is specified as the final recommended imaging start timing.

For example, assuming the position of point Rp as the first specific phase in the electrocardiographic waveform of FIG. 3 in the heartbeat information, and the maximum inhalation time B1 as the second specific phase in the breathing information, the time point at which they overlap is assumed as the recommended imaging start timing.

<1-2-1-2-4. Recommended Imaging End Timing Specifying Method: Prediction>

The first recommended imaging end timing specifying method is applicable to both the simple phase control and the two-way phase control, and is a method that assumes the time point at which a predetermined time has elapsed, with the recommended imaging start timing specified based on the heartbeat phase and/or the respiratory phase obtained by the detecting section 110 as a starting point, as the recommended imaging end timing. This time (imaging continuous time) may be defined with an absolute time (time in units of seconds), or be set to a time obtained by determining the number of seconds in one period of the heartbeat (or breathing) by actual measurement and calculating the time for a predetermined number of times of the relevant period. By way of example, if the heartbeat period of the test subject M is actually measured as 0.75 seconds on an average according to the actual measurement by the electrocardiographic monitor 4, 0.75×3=2.25 seconds, which is for three periods, can be assumed as the imaging continuous time. The X-ray image of a plurality of frames is acquired by the X-ray irradiation of repeated pulse-shape during the period of the imaging continuous time as will be described later, but a predetermined multiples of the repeated period of the X-ray irradiation may be assumed as the imaging continuous time.

According to the above combinations, a shorter value of the first imaging continuous time specified with the absolute time and the second imaging continuous time value calculated with integral multiples of the period of the heartbeat (or breathing) may be set as the final imaging continuous time. This combination, in other words, corresponds to the forcible ending of the imaging before exceeding the upper limit threshold value, the upper limit threshold value being the integral multiples of the period of the heartbeat (or breathing), while specifying the imaging continuous time with the absolute time.

Meanwhile, the recommended imaging end timing may be determined based on the real time measurement with the actual start of imaging as a trigger. In other words, the above descriptions are both based on the idea of predicting or estimating the time until the necessary imaging is completed since the imaging continuous time is set using the absolute time or the heartbeat (breathing) period determined in the actual measurement in the past, but are methods of ending the imaging when the heartbeat or the breathing reaches a predetermined phase while continuously monitoring the state of the heartbeat and the breathing of the test subject M. Specifically, this is performed with second or third recommended imaging end timing specifying method described below.

The first recommended imaging end timing specifying method is not the sole case, and if the recommended imaging end timing is defined with the temporal starting point for the specification of the recommended imaging end timing as the timing to start imaging, such starting point may be the recommended imaging start timing or may be the actual imaging start timing (i.e., timing at which the imaging is actually started based on the operation of the photographer).

<1-2-1-2-4-1. First Variant of Recommended Imaging End Timing Specifying Method>

The variant of the recommended imaging end timing specifying method corresponds to the simple phase control, and uses the heartbeat information detected with the heartbeat information detection method by the detecting section 110.

In other words, the recommended imaging end timing is specified on the basis of the phase detection based on the detection of the electrocardiographic waveform. For example, a method for specifying the recommended imaging end timing with a time point of point Tp as the specific phase in the electrocardiographic waveform of FIG. 3, a method for counting the number of periods from the imaging start timing and determining the end position, and the like are known.

The mode of using the heartbeat period is similar to the previously described prediction setting, but the calculation is carried out using the heartbeat period calculated from the actual measurement in the past in the prediction setting whereas the elapse of the heartbeat period is monitored by the actual measurement in real time in this mode, and thus the setting of a more accurate imaging end timing can be made than the prediction control.

<1-2-1-2-4-2. Second Variant of Recommended Imaging End Timing Specifying Method>

Another variant of the recommended imaging end timing specifying method corresponds to the simple phase control, and uses the heartbeat information detected with the breathing information detection method by the detecting section 110.

In other words, the recommended imaging end timing is specified on the basis of the phase detection based on the measurement result by the cycle detection sensor 15 or another device.

For example, a method for acquiring the period of breathing after the start of imaging, and specifying the position where the motion of breathing of N periods is terminated as the recommended imaging end timing, and the like is known.

<1-2-1-3. Notification Information Generating Section 130>

In the notification information generating section 130 of FIG. 2, the notification information for notifying the photographer of the recommended imaging timing is generated based on the information of the periodic changes of the heart (lung) of the test subject M detected by the detecting section 110 and the recommended imaging timing specified by the recommended imaging timing specifying section 120. The generated notification information is output to the notifying section 240.

As previously described, the concept of "recommended imaging timing" includes at least the "recommended imaging start timing" for urging the imaging start operation on the photographer but may also include the "recommended imaging end timing" for urging the imaging end operation on the photographer.

Generally, the mode when not making the notification of the "recommended imaging end timing" includes two modes:

1) Automatically ending the imaging at a time at which the imaging continuous time, which is set based on the prediction or the actual measurement described above, has elapsed from the recommended imaging start timing (or actual imaging start timing);

2) Solely leaving to the decision of the photographer, and ending the imaging in response to the ending operation of the photographer.

The mode when making the notification of the "recommended imaging end timing" is the mode in which 3) The system performs the notification of the recommended imaging end timing with respect to the photographer when the imaging continuous time, which is set based on the prediction or the actual measurement previously described, is reached from the recommended imaging start timing, and the photographer ends the imaging in response to the notification.

Among the above, the notification of the recommended imaging end timing in the case of 3) can be made in a substantially similar form to the notification of the recommended imaging start timing described below, where the difference essentially lies on at what time point to make the notification. As a matter of course, in making the notification of the recommended imaging end timing, the notification is preferably made in a form sensuously different from the notification of the recommended imaging start timing (e.g., in the case of the visual notification to be described later, indicators of colors in different series are used, etc.).

The category and the specific example of the notification information of the recommended imaging start timing are shown below, where the information of at least one of "visual notification information for checking visually" and "auditory notification information for checking aurally" is included.

The modes of the visual notification information and the auditory notification information will be sequentially described below focusing on the recommended imaging start timing, but the matters that do not essentially depend on the difference of whether the start or the end of imaging can be similarly applied for the recommended imaging end timing.

<1-2-1-3-1. Visual Notification Information>

In the notification information generating section 130, the visual notification information shown below is generated for the notification information, and visually displayed on a screen of a display (e.g., color liquid crystal display) configuring the display unit 34 (FIG. 1 and FIG. 2).

For example, the visual notification information for making the notification of the recommended imaging start timing may include an indicator for displaying, in a step wise manner, the proximity degree to the recommended imaging start timing. The indicator to create here is a progress bar display, display by numerical values, display by model diagram, display by period diagram, and the like, and is preferably displayed on a screen in a mode that the approach of the recommended imaging start timing can be known before the recommended imaging start timing is actually reached so that the photographer can recognize the recommended imaging start timing well in advance (specific example will be described later). The peak display of the indicator may be created so that the peak is obtained at the recommended imaging start timing or may be created to display the movement of the phase information as is.

In other words, in the notification information generating section 130, the information of the recommended imaging start timing specified by the recommended imaging timing specifying section 120 is generated as the indicator or the expressive element with the periodic information or the phase information detected by the detecting section 110.

Figure 7:
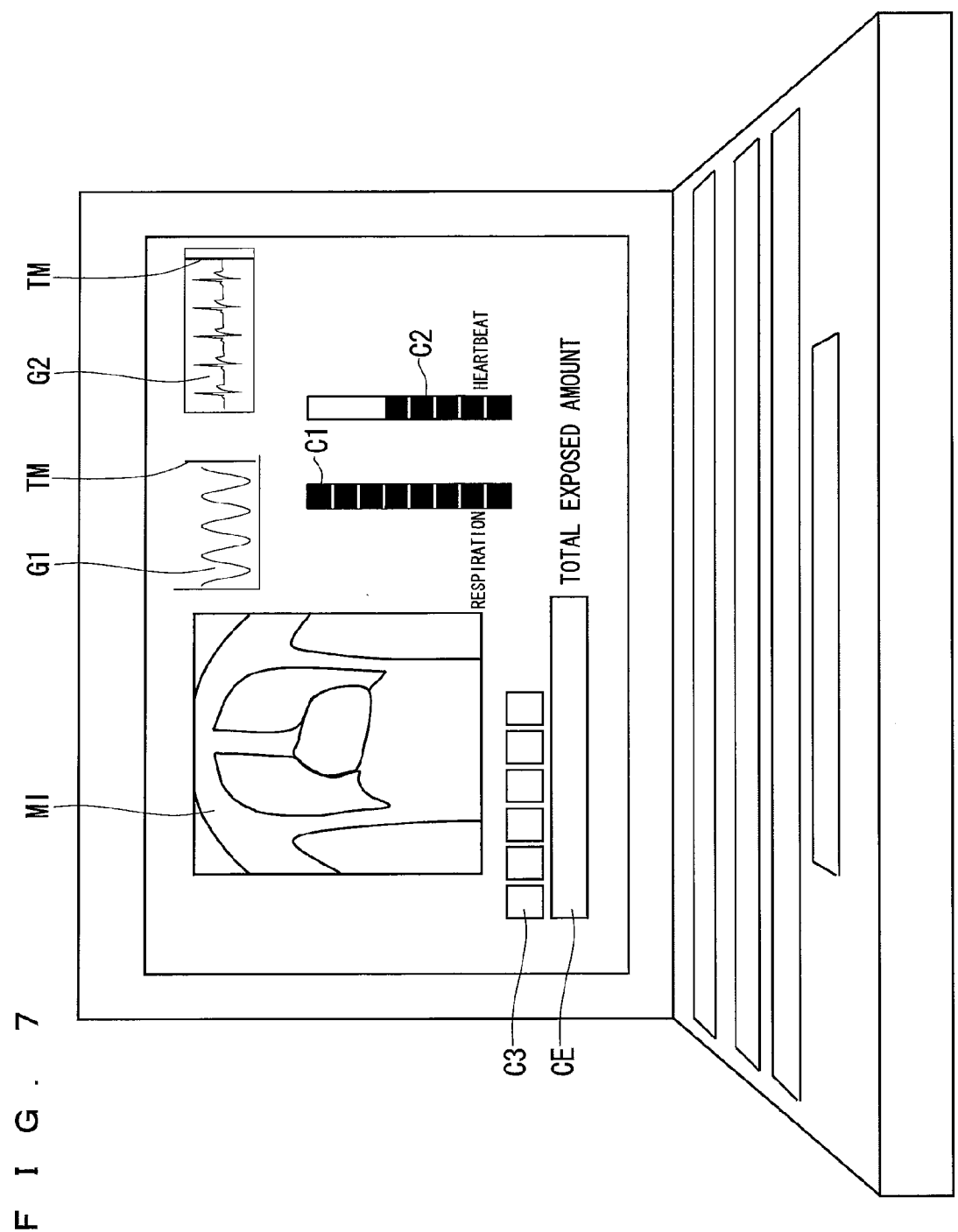
FIG. 7 is a schematic view showing graphics and model diagram generated as auditory notification information in association with each other.

FIG. 7 shows an example generated as the visual notification information and displayed on a screen of a display of the display unit 34. As shown in FIG. 7, other than an X-ray image MI imaged for the test subject M, the following are displayed in parallel on the screen as graphic elements:

Respiratory diagram G1 expressing the respiration cycle,
Electrocardiogram G2 indicating the electrocardiographic waveform,
Level meter C1 corresponding to the respiratory phase,
Level meter C2 corresponding to the heartbeat phase,
Level meter (color bar) C3 in which both the heartbeat phase and the respiratory phase are integrated, and
Progress bar CE expressing the total exposed amount of the test subject M up to the current time point.

The phase position at the current time point detected by the detecting section 110 is indicated with a line TM in the respiration diagram G1 and the electrocardiogram G2. The line TM moves toward the right side on the respective waveform chart with elapse of time (therefore, change in phase), jumps to the left end when reaching the right end, and again moves toward the right side.

Figure 5:
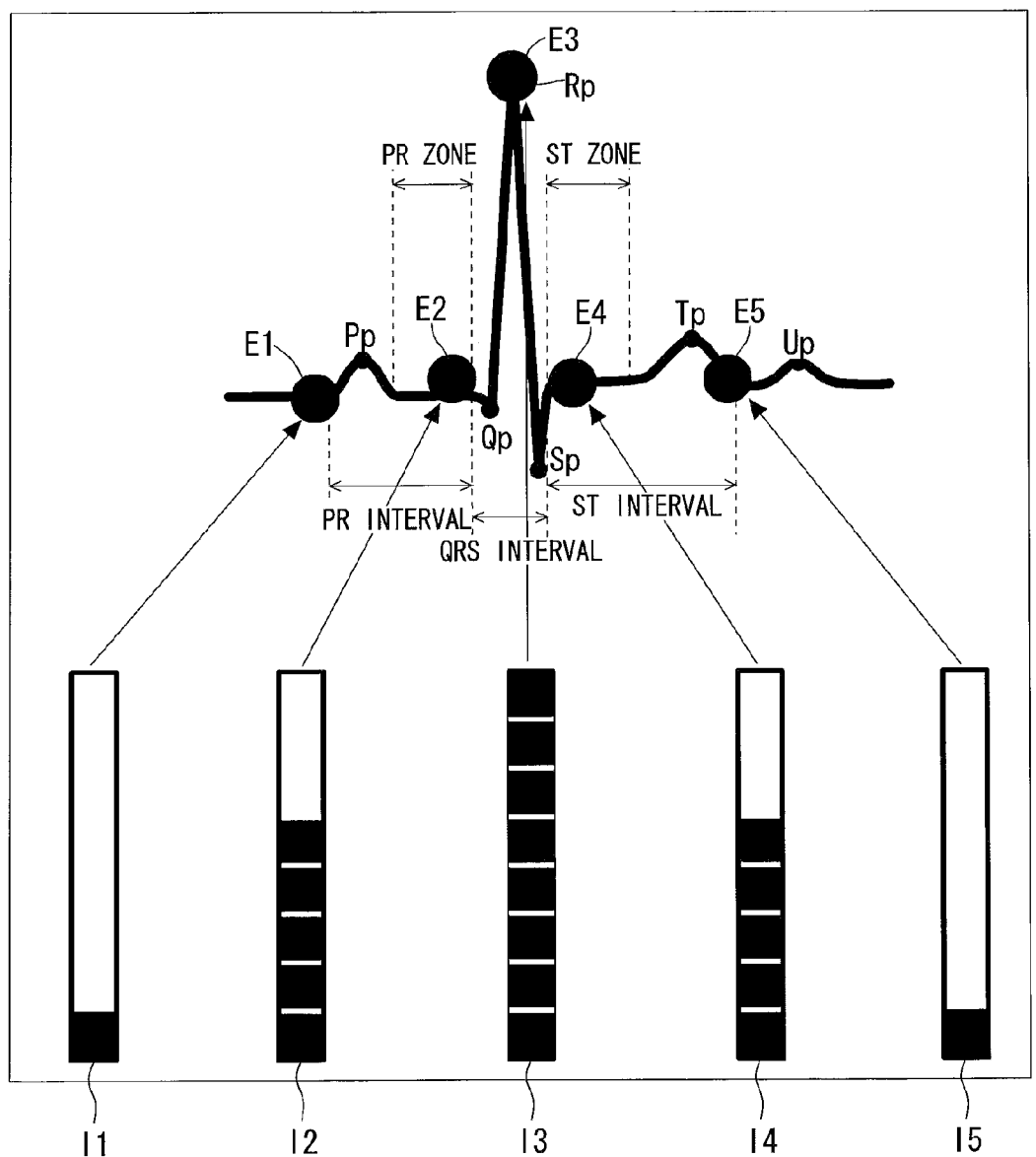
FIG. 5 is a view showing an indicator and an expressive element generated in correspondence with the electrocardiographic waveform.

FIG. 5 is a view illustrating a representation rule of the level meter C2 showing the recommended imaging start timing in correspondence with the electrocardiographic waveform. The representation states I1 to I5 indicate the statuses of the level meter C2 at time points corresponding to the phases E1 to E5 of the electrocardiographic waveform, respectively. As shown in FIG. 5, the number of indices in the level meter C2 gradually increases in the PR zone or the PR interval, for example, and the number of indices becomes a maximum in the representation state I3 at the position of point Rp. On the other hand, the number of indices of the representation states I4 and I5 gradually reduces in the ST zone or the ST interval. The level meter C2 may be generated such that the number of indices becomes a maximum at the position of point Pp, and the number of indices becomes a minimum at the position of point Tp or point Up.

A unit index element (small rectangle in the illustrated example) included in the level meter C2 has different color states for each individual index element. For example, the lowest representation index in the level meter C2 has a light red color, the highest representation index has a dark red color, and the unit index elements between the two have a red color in which the brightness sequentially changes in a gradation form.

Figure 6:
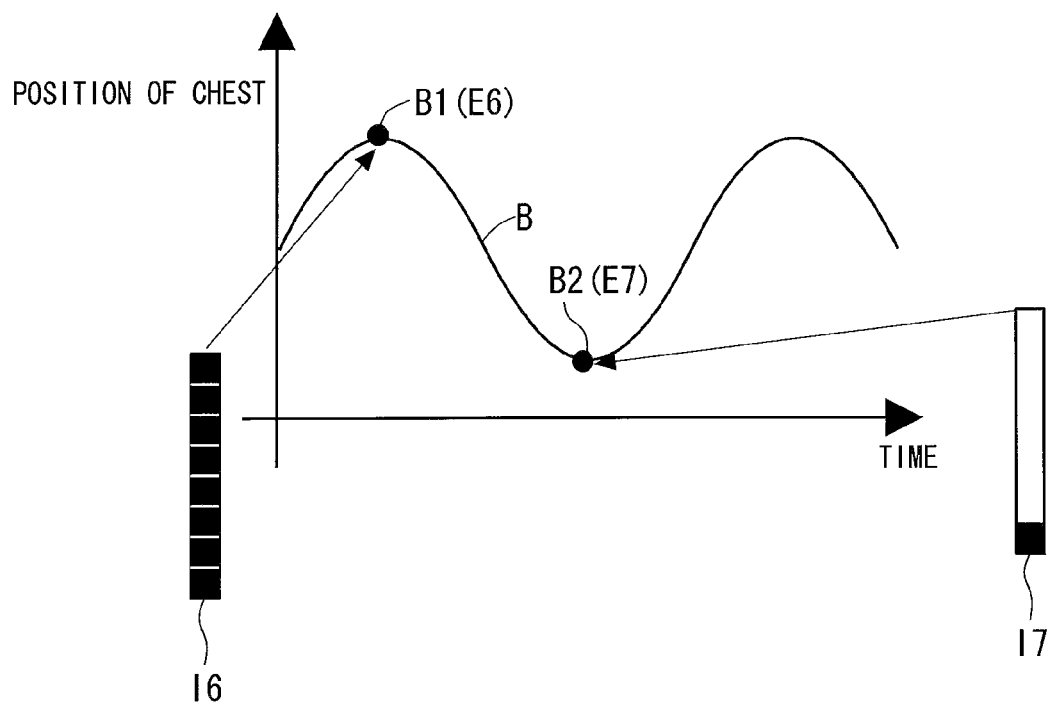
FIG. 6 is a view showing an indicator and an expressive element generated in correspondence with the temporal change in the detection information of the cycle detection device 16.

FIG. 6 is a view illustrating the representation rule of the level meter C1 (FIG. 7) generated in correspondence with the respiration cycle B detected from the cycle detection device 16. In other words, the number of indices in the level meter C1 becomes the maximum and the minimum at the phases E6 and E7, respectively, corresponding to the maximum inhalation time B1 and the maximum exhalation time B2 in the change in the detection information detected by the detecting section 110. The representation index in the level meter C1 increases or decreases in the phase zone in between.

The level meter C1 preferably uses a color system (e.g., gradation of blue color system) of a hue different from the other level meter C2 for the purpose of facilitating the distinction with the other level meter C2.

In the screen display of FIG. 7, the level meter C3 in which both the heartbeat phase and the respiratory phase are integrated is a color bar representing the multiplication value (comprehensive recommended imaging start timing) of the respective index values of the level meters C1 and C2, for example. For example, the unit index element (small rectangle) at the left end of the index bar C3 is blue, the unit index element at the right end is red, and the hue is changed sequentially from blue to red in between. The level meter C3 is a bar of variable length that is in a longest state of being entirely displayed at the phase coinciding with the comprehensive recommended imaging start timing, and the level meter C3 sequentially becomes shorter away therefrom so that only the blue side is displayed.

The representation modes of the level meters C1, C2, and C3 can be variously deformed, where the evaluation level of having the current time point as the imaging start timing can be represented with various visual elements such as color, difference in shading, long and short (color or shading of the visual notification information is changed according to the proximity degree to the recommended imaging start timing).

Figure 8:
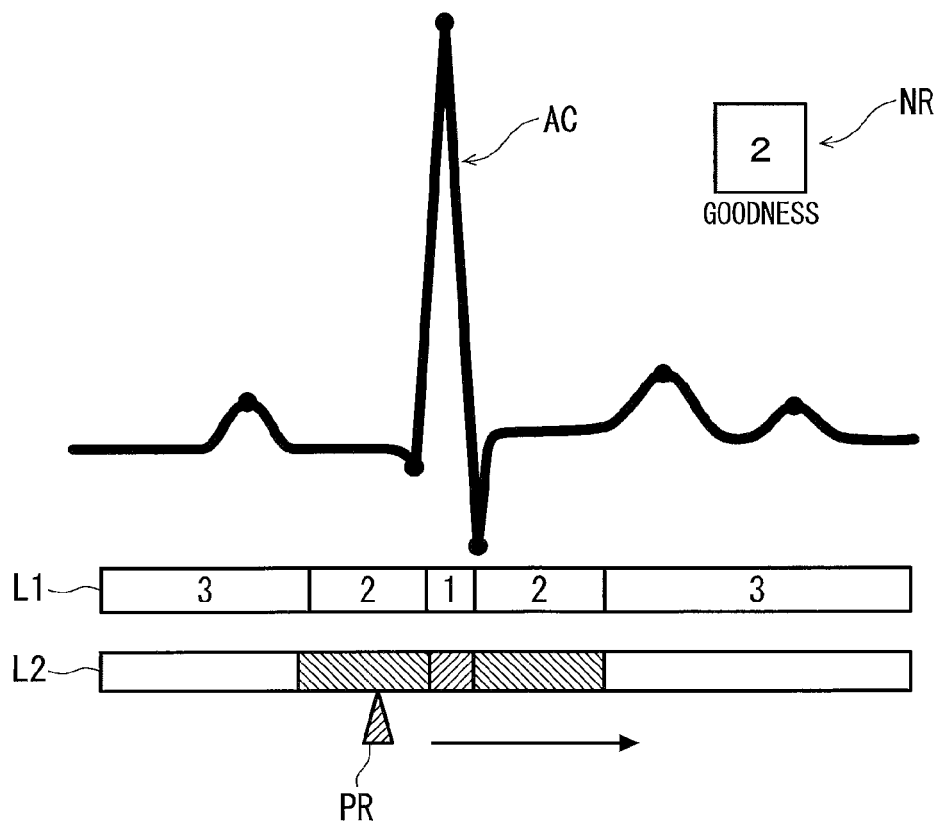
FIG. 8 is a view showing other graphics display modes of a screen of a display of a display unit.

FIG. 8 is a view showing another graphic display mode of the screen of the display of the display unit 34. The waveform of the electrocardiogram is graphic displayed, and two bands extending in the phase direction (time direction) of the electrocardiogram are displayed at the lower part thereof. An evaluation level in which the goodness on whether it is preferable to start the imaging at the relevant phase is numerically represented is additionally displayed in each region and visually represented in correspondence with each phase of the heart beat in the band L1 on the upper side. In the illustrated example, the evaluation level is additionally described in three stages of "1" to "3" in order from the most preferred phase range. The evaluation level is also represented in shading of the color of the band 12 on the lower side. At which position in the phases the current time point is at is variable displayed with the position of a moving pointer PR. In the illustrated example, the pointer PR is in the range of the evaluation level "2", but since the pointer PR moves in the right direction (direction of arrow in the figure) with elapse of time, the photographer can intuitively recognize that the phase range of evaluation level "1" can be reached in just a small amount.

Both are visual information in which the first expressive element (e.g., bands L1 and L2) visually expressing the evaluation level with respect to having the respective phase as the imaging start timing, and the second expressive element (e.g. pointer PR) indicating to which phase the current time point corresponds in real time are given in the graphics display expressing the periodic temporal changes of the heart.

The evaluation level can also be numerically displayed in a numerical value expression frame NR. In other words, the notifying section 240 can also display the numerical information corresponding to the proximity degree to the recommended imaging start timing.

In FIG. 8, a plurality of visual notification modes are combined for the purpose of explaining various visual notification modes of the recommended imaging start timing, but only one of the modes (e.g., display only the band L2 and the pointer PR in association with the electrocardiographic waveform) may be provided.

Figure 9:
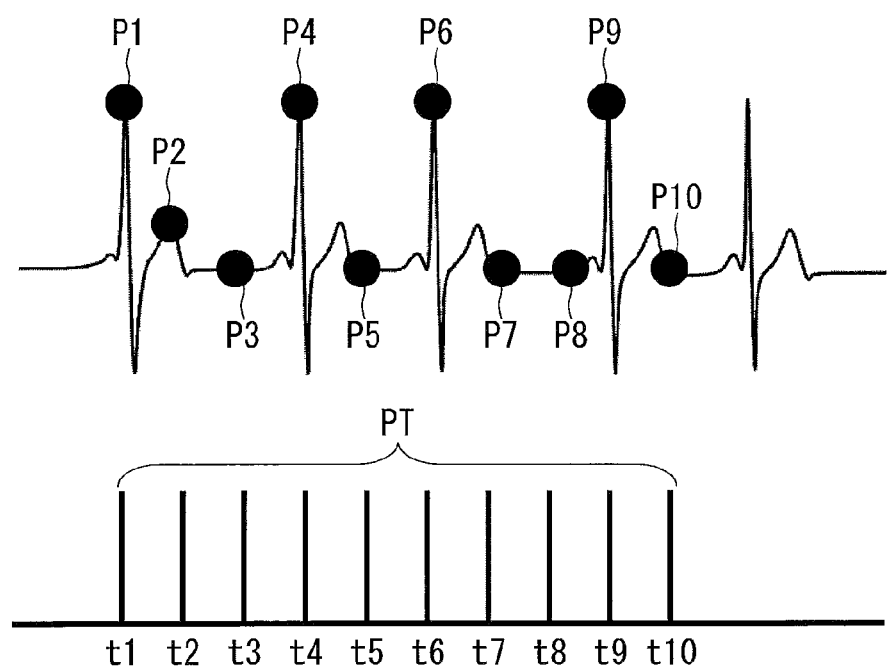
FIG. 9 is a view showing an example in which imaging points after the start of imaging are given to the electrocardiographic waveform.

FIG. 9 is a view showing an example in which an imaging point after the start of imaging is given to the electrocardiographic waveform, where such graphics can be displayed in accordance with the screen of the display of the display unit 34.

In the dynamic radiographic imaging system 100 of the present embodiment, when the photographer performs the imaging start operation '(instruction input), the X ray is irradiated in the mode of a periodic repeated pulse, and one X-ray image is acquired as a frame image for every irradiation pulse. The imaging start timing in such imaging corresponds to the timing of instructing the start of irradiation of the first pulse of a series of pulses, and the imaging end timing corresponds to the timing of instructing the end of irradiation of the series of pulses. Therefore, the recommended imaging start timing refers to the recommended timing serving as time t=t1 in FIG. 9, and the recommended imaging end timing refers to the recommended timing serving as time t=t10.

As shown in FIG. 9, the imaging points (X-ray irradiation pulse generation time) P1 to P10 corresponding to the imaging timing PT are visually displayed by being added on the electrocardiographic waveform. Specifically, in synchronization with the imaging timing PT at time t=t1, t2, t3, . . . , and t10, the graphics elements (black dot in the illustrated example) indicating the imaging points P1, P2, P3, . . . , and P10 are respectively added on the electrocardiographic waveform. Thus, whether or not the imaging is carried out at the desired timing can be checked.

Thus, in the notification information generating section 130, one or a plurality of the various visual notification information described above is generated and displayed on the screen of the display of the display unit 34. When performing the two-way phase control, the timing at which the first specific phase and the second specific phase overlap may be generated as the easily recognizable visual notification information such as flashing display.

<1-2-1-3-2. Auditory Notification Information>

In the notification information generating section 130, the auditory notification information is also generated to make the notifications of the periodic changes detected by the detecting section 110 and the information of the recommended imaging timing specified by the recommended imaging timing specifying section 120. The auditory notification information includes buzzer and timing sound, audio, and the like. For example, a method of announcing the seconds until the recommended imaging start timing with a synthesized sound, a method of changing the volume and tone in multiple stages as the recommended imaging start timing approaches, and sounding the buzzer or the timing sound, and the like are known.

When performing the two-way phase control, the timing at which the first specific phase and the second specific phase overlap may be generated as the auditory notification information different from the simple phase control.

<1-2-1-4. Notifying Section 240>

In the notifying section 240 arranged in the display unit 24 of FIG. 2, the visual notification information generated by the notification information generating section 130 is displayed on the screen of the display of the display unit 34 in multiple stages as the recommended imaging timing approaches to notify the photographer of the timing thereof.

In other words, the notifying section 240 is configured to include a notifying section that makes the notification to the photographer in multiple stages as the recommended imaging start timing approaches, and a second notifying section that makes the notification to the photographer in multiple stages as the recommended imaging end timing approaches.

In the notifying section 240 according to the present embodiment, the notifications of all the graphic elements shown in FIG. 7 are assumed to be made, and the notification information includes both the visual notification information and the auditory notification information. Therefore, the photographer is notified of the auditory notification information by generating sound information from the sound source in synchronization with the visual notification information.

The photographer takes into consideration the time lag from when receiving the notification on the recommended imaging timing (recommended imaging start timing or recommended imaging end timing) until performing the imaging operation, and the notifying section 240 preferably makes the notification of the notification information at a timing slightly earlier than the respective recommended imaging timing. Such preceding time can be set by experimentally obtaining in advance the time required for the response of the photographer from when receiving the notification, and storing such time in the notifying section 240 in advance.

The recommended imaging start timing has been mainly described above, but the mode may be switched to the mode of "end notification" while using the visual or auditory expression for start notification after the start of imaging when also making the notification of the recommended imaging end timing. In such period, the evaluation level at the start of imaging, for example, is replaced with the evaluation level at the end of imaging. Between "start" and "end", differing the color for the case of visual display, the tone color for the case of auditory display by electronic sound, and the like is useful for the photographer to distinguish the effect of notification. Since "notification of start" and "notification of end" do not occur at the same time, the limited screen can be efficiently used by temporally switching as described above rather than displaying in parallel the graphic element for the "notification of start" and the graphic element for the "notification of end" in one screen.

<1-2-1-5. Imaging Capturing Control Section 140>

In the image capturing control section 140 of FIG. 2, the imaging is started in response to the instruction input from the photographer who received the notification information (notification of recommended imaging start timing etc.) by the notifying section 240. In other words, when the photographer, who received the notification information, manually operates the operation unit 23 to make an instruction input, the image capturing control section 140 performs a control with respect to the radiation irradiation control device 12 and gives a command such as to start the imaging.

In other words, the operation unit 23 is configured to include an operation unit that receives the instruction input from the photographer for starting the radiation imaging of the subject M, and a second operation unit that receives the instruction input from the photographer for ending the radiation imaging of the subject M.

The image capturing control section 140 is configured to include an imaging control unit that performs the starting of the radiation imaging of the subject M in response to the instruction input by the operation unit, and the second imaging control unit that performs the ending of the radiation imaging of the subject M in response to the instruction input by the second operation unit.

<1-2-2. Basic Operation of Dynamic Radiographic Imaging System 100>

Figure 10:
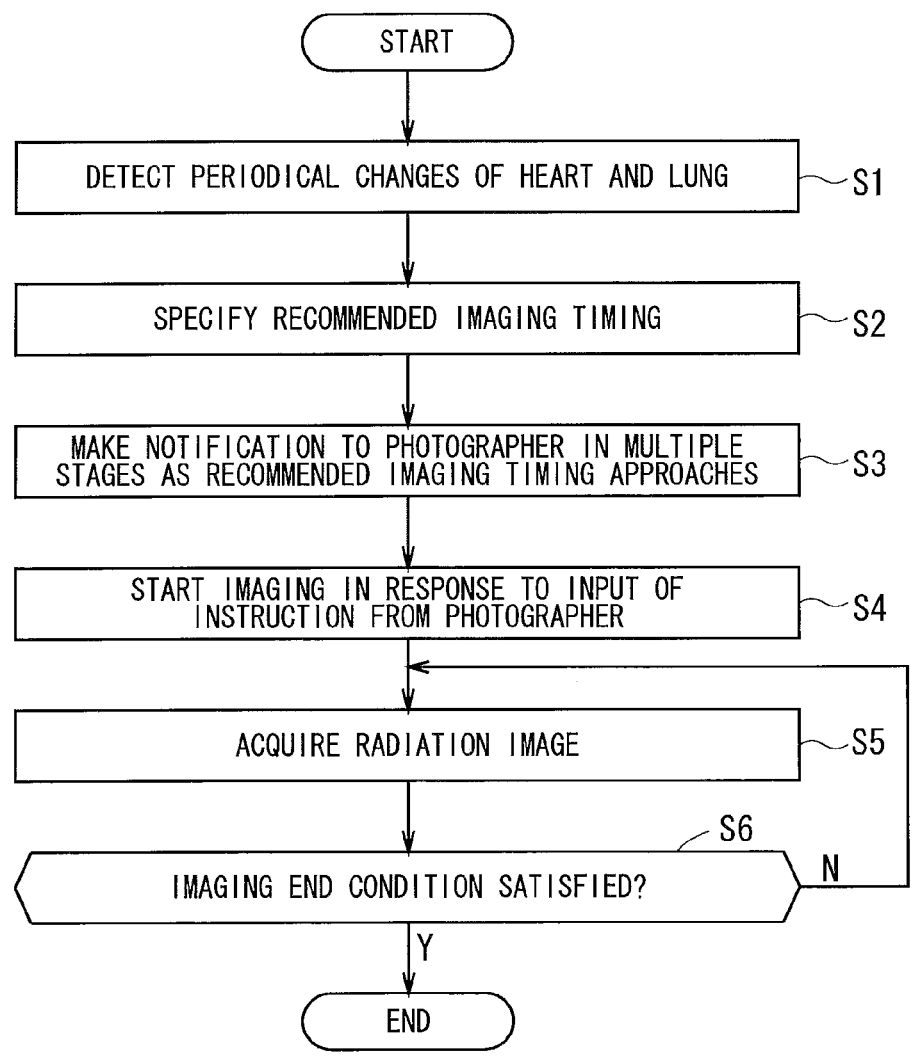
FIG. 10 is a flowchart describing a basic operation realized in the dynamic radiographic imaging system 100 according to the first embodiment.

FIG. 10 is a flowchart for describing the basic operation realized in the dynamic radiographic imaging system 100 according to the present embodiment. The description of the individual function of each unit has already been made (see FIG. 2), and hence only the overall flow will be described herein.

As shown in FIG. 10, the detecting section 110 of the control unit 21 first detects the periodic changes of the geometric configuration of the heart and the lung in step S1 (see FIG. 2). Specifically, the heartbeat information is detected based on the result acquired from the phase detecting section 41 of the electrocardiographic monitor 4, and the breathing information is detected based on the result acquired from the cycle detection sensor 15 (see FIG. 1).

In step S2, the recommended imaging timing specifying section 120 specifies the recommended imaging timing in the future based on the detection result of step S1 in the detecting section 110 (see FIG. 2). Specifically, one of the first to third recommended imaging start timing specifying methods can be adopted for the specification of the recommended imaging start timing, and one of the imaging end timing specifying methods described above can be adopted for the specification of the recommended end timing.

In step S3, the notifying section 240 displays the notification information (see FIG. 5 to FIG. 9) generated by the notification information generating section 130 on the display unit 24 at a time corresponding to the recommended imaging start timing to make the notification to the photographer in multiple stages as the recommended imaging start timing approaches (see FIG. 2). The photographer perceives the notification and performs the imaging start operation on the operation unit 33.

In the case of the indicator display of FIG. 7 described above, the indicator itself is visually displayed continuously, where the display of the level of the evaluation degree becomes a maximum when an optimum imaging start timing is reached at a time corresponding to the recommended imaging start timing. The photographer visually recognizes that such maximum level is reached, and performs the imaging start operation on the operation unit 33 in synchronization therewith.

In step S4, the image capturing control section 140 gives a command to the radiation irradiation control device 12 so as to start imaging in response to the instruction input from the photographer who received the notification information (see FIG. 2). In response thereto, the X-ray irradiation in the mode of a series of pulses as shown in FIG. 9 is started.

In step S5, the reading control device 14 that received the synchronization signal from the radiation irradiation control device 12 provides an output command signal to the image capturing unit 13 to output an electric signal from the respective unit element (pixel) of the image capturing unit 13. The image data for one frame is acquired as a collection of electric signals from each pixel for one pulse of the X-ray, and the acquired image data is output to the imaging console 2 and stored in the storage unit 22 (see FIG. 1).

In step S6, whether or not the imaging end conditions are satisfied is determined. In other words, if configured to automatically define the imaging end timing with the imaging start timing as the starting point, whether or not the imaging end timing is reached is determined, where the present operation flow is terminated if the imaging end timing is reached and the process returns to step S5 if not reached to perform the generation of the next X-ray pulse and the imaging of the next frame.

When the instruction to end the imaging is made through the manual operation in response to the notification of the recommended imaging end timing, the photographer operates the operation unit 33 in response to the notification of the recommended imaging end timing to perform the imaging end operation, and the image capturing control section 140 performs the imaging end process in accordance therewith to leave the repeating loop. Even if the notification of the recommended imaging end timing is not made, the repeating loop can be left and the present operation flow can be terminated if the photographer performs the imaging end operation on the operation unit 33.

Thus, in the dynamic radiographic imaging system 100, the photographer can easily grasp the appropriate imaging timing by making the notification to the photographer in multiple stages as the recommended imaging timing defined from the detection result of the time change of a predetermined site approaches, so that the convenience of the photographer enhances. Thus, the imaging start timing can be accurately determined even when the heartbeat and the respiration period are not regular and even by the unskilled person, and a more appropriate medical decision can be made.

2. Second Embodiment

Figure 11:
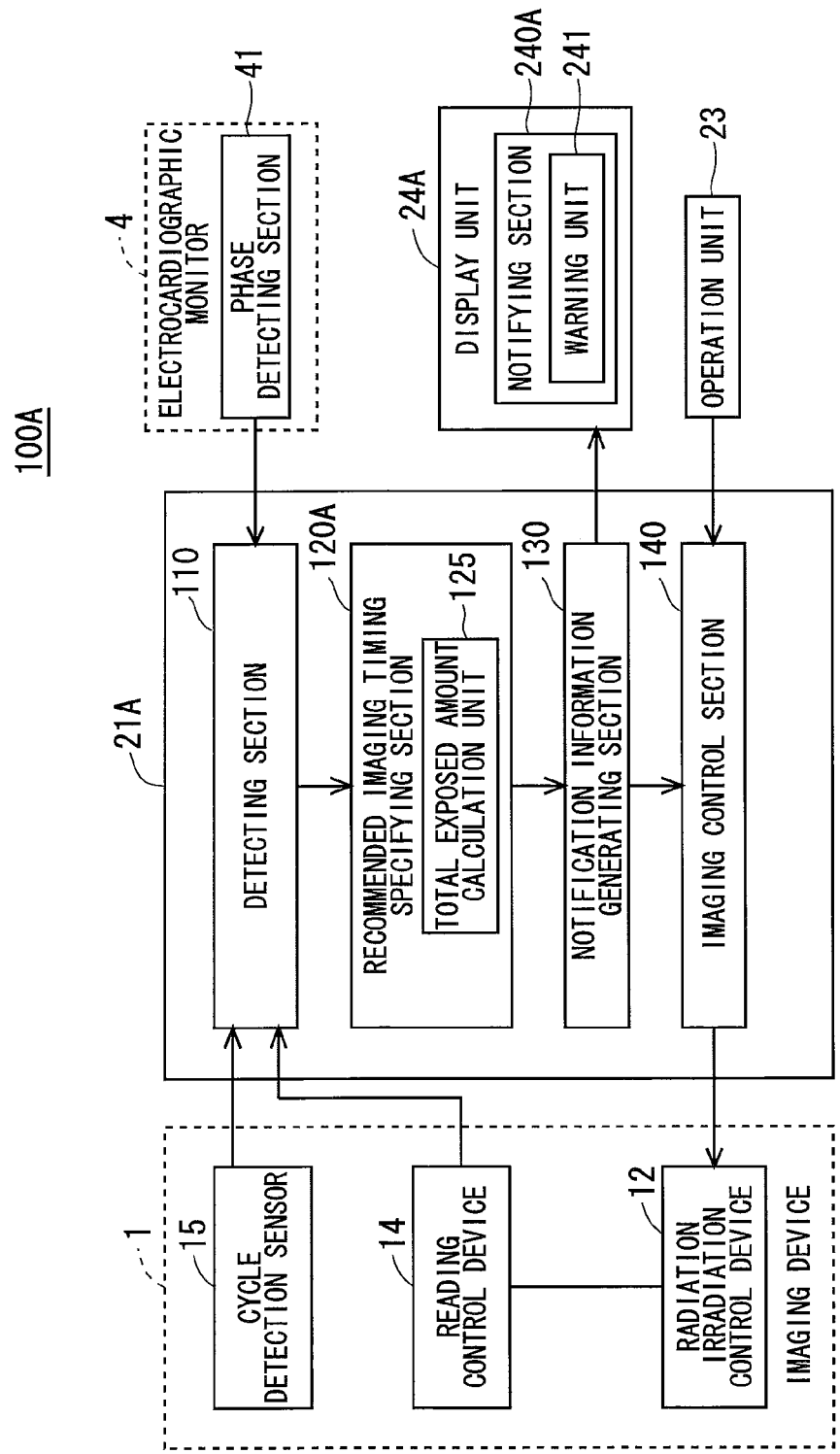
FIG. 11 shows a block diagram showing a function configuration of a dynamic radiographic imaging system 100A according to a second embodiment.

FIG. 11 is a view showing a function configuration of a control unit 21A and a display unit 24A used in a dynamic radiographic imaging system 100A (FIG. 1) configured as a second embodiment of the present invention. The control unit 21A and the display unit 24A are respectively used as alternatives of the control unit 21 and the display unit 24 (FIG. 2) in the system 100 of the first embodiment. The difference from the first embodiment is that a recommended imaging timing specifying section 120A includes a total exposed amount calculation unit 125, and a notifying section 240A of the display unit 24A includes a warning unit 241. The remaining configuration is similar to the system of the first embodiment.

In the total exposed amount calculation unit 125, the total exposed amount of the test subject M at the time of imaging is calculated. Thus, when specifying the recommended imaging end timing, the recommended imaging timing specifying section 120 may taken into consideration the calculation result by the total exposed amount in addition to the first to third imaging end timing specifying methods.

In the warning unit 241, the end of imaging is warned to the photographer when the parameter reflecting the total amount of radiation irradiation after the start of imaging satisfies a predetermined condition. Here, the warning when the total exposed amount exceeds a determination threshold is generated as the visual notification information or the auditory notification information by the notification information generating section 130.

<2-1. Basic Operation of Dynamic Radiographic Imaging System 100A>

Figure 12:
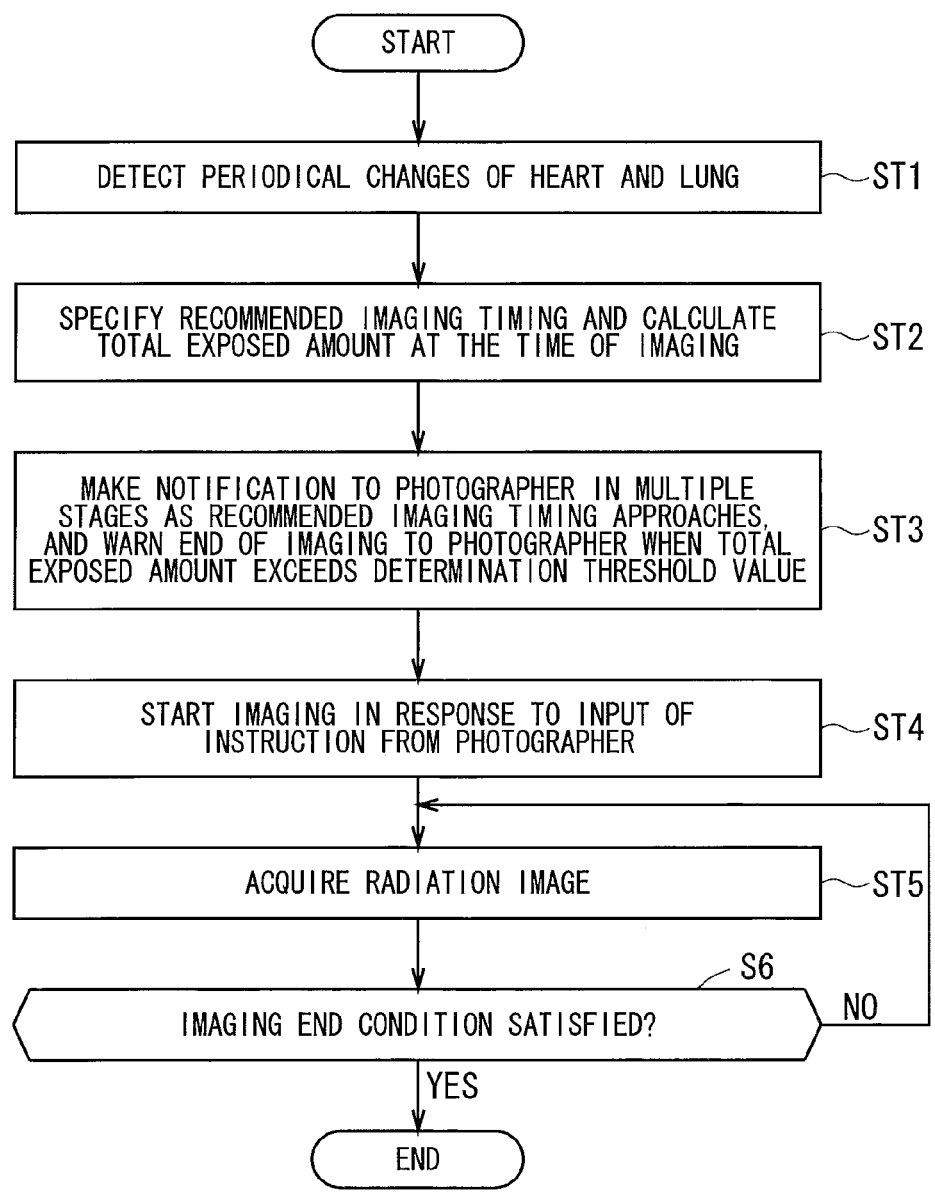
FIG. 12 is a flowchart describing a basic operation realized in the dynamic radiographic imaging system 100A according to the second embodiment.

Then, FIG. 12 is a view showing an operation flow of the dynamic radiographic imaging system 100A according to the second embodiment. In FIG. 12, steps ST1, ST4, ST5, and ST6 are similar to steps S1, S4, S5, and S6 of FIG. 10, and hence the description thereof will be omitted.

In the second embodiment, the following steps are added due to the addition of the total exposed amount calculation unit 125 and the warning unit 241, which did not exist in the first embodiment.

In other words, as shown in FIG. 12, in step ST2, the recommended imaging timing specifying section 120 specifies the recommended imaging timing in the future based on the detection result of the detecting section 110 and the total exposed amount calculation unit 125 estimates and calculates the total exposed amount serving as a sum of an accumulated exposed amount received by the test subject M within a predetermined period in the past and an estimated exposed amount received by the test subject M when receiving the X-ray irradiation of repeated pulses over a predetermined imaging continuous time this time. The accumulated exposed amount in the past is stored in the storage unit 32 in the system 100A for every test subject or the server on a medical network in the hospital where the system 100 is installed, and is used by being read out.

In step ST3, the notifying section 240 makes the notification to the photographer in multiple stages as the recommended imaging timing approaches by the notification information generated by the notification information generating section 130. If the total exposed amount after the start of imaging is assumed to exceed a predetermined determination threshold value (more generally, if the parameter reflecting the total amount of radiation irradiation is assumed to satisfy a predetermined condition), the warning unit 241 warns the photographer and recommends to cancel imaging. However, warning is merely made in the present embodiment taking into consideration that the merits of performing imaging are greater even if the total exposed amount exceeds a predetermined threshold value. The warning may be made by visual display by the display unit 34 or may be made by auditory display. For example, a current value of the progress bar CE of FIG. 7 represents the total exposed amount up to the relevant time point, but for example, if the total exposed amount is about to exceed the threshold value any minute, the entire display of the progress bar CE may be discontinuously flashed and the electronic sound may be emitted to make the warning.

ST4 and ST5 are performed as steps similar to the first embodiment, and then the present operation flow is terminated.

If the total exposed amount does not exceed a predetermined threshold value until the middle of the series of imaging, the imaging is repeated up to such stage and the warning is again made immediately before exceeding the threshold value. In this case, whether or not the total exposed amount exceeds the threshold value with the pulse of next time is determined each time before returning to step ST4 from step ST6, and the warning is again made when the total exposed amount exceeds the threshold value. The value of the total exposed amount is updated for each imaging of one frame image with the progress of imaging. The imaging can be carried out up to the last point of being smaller than or equal to the threshold value by performing continuous monitoring and warning of the total exposed amount, but only partial information (dynamic image up to the middle) are acquired for the dynamic image.

Thus, in the dynamic radiographic imaging system 100A, the decision to cancel the series of imaging or to cancel in the middle even if the series of imaging is started can be easily made by displaying the information of the total exposed amount. Thus, the excessive exposure to be received by the test subject M can be prevented. Furthermore, the imaging necessary and sufficient for diagnosis can be realized even by an unskilled person by automatically warning the end of imaging to the photographer.

<3. Third Embodiment>

Figure 13:
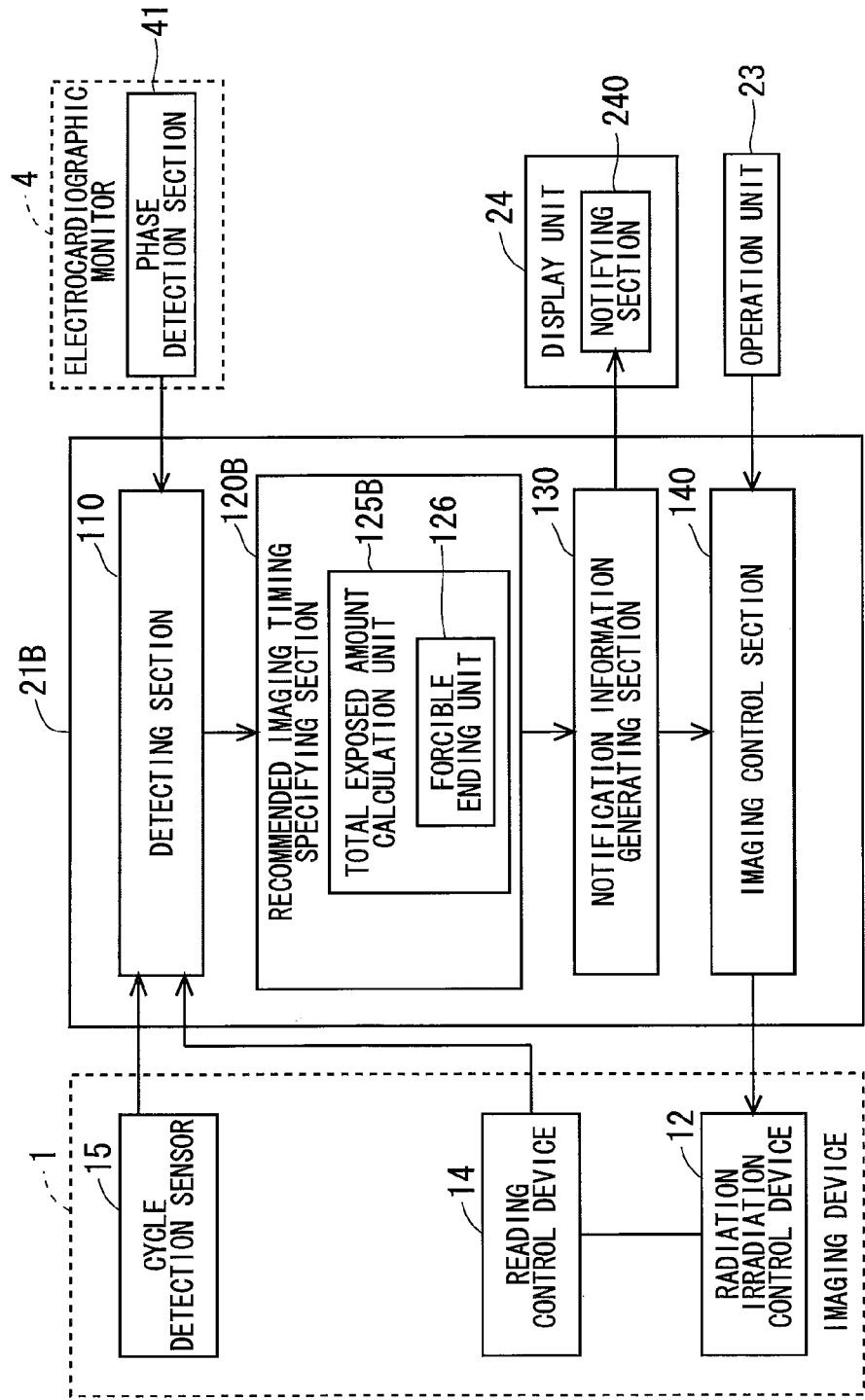
FIG. 13 shows a block diagram showing a function configuration of a dynamic radiographic imaging system 100B according to a third embodiment.

FIG. 13 is a view showing a function configuration of a control unit 21B used in a dynamic radiographic imaging system 100B (FIG. 1) configured as a third embodiment of the present invention. The control unit 21B is used as an alternative of the control unit 21 (FIG. 2) in the system 100 of the first embodiment. The difference from the first embodiment is that a total exposed amount calculation unit 125B and a forcible ending unit 126 are arranged in a recommended imaging timing specifying section 120B. The remaining configuration is similar to the system 100 of the first embodiment.

The total exposed amount calculation unit 125B has a similar function as the total exposed amount calculation unit 125 of the second embodiment.

In the forcible ending unit 126, the imaging is forcibly ended when the parameter reflecting the total amount of radiation irradiation after the start of imaging satisfies a predetermined condition.

<3-1. Basic Operation of Dynamic Radiographic Imaging System 100B>

Figure 14:
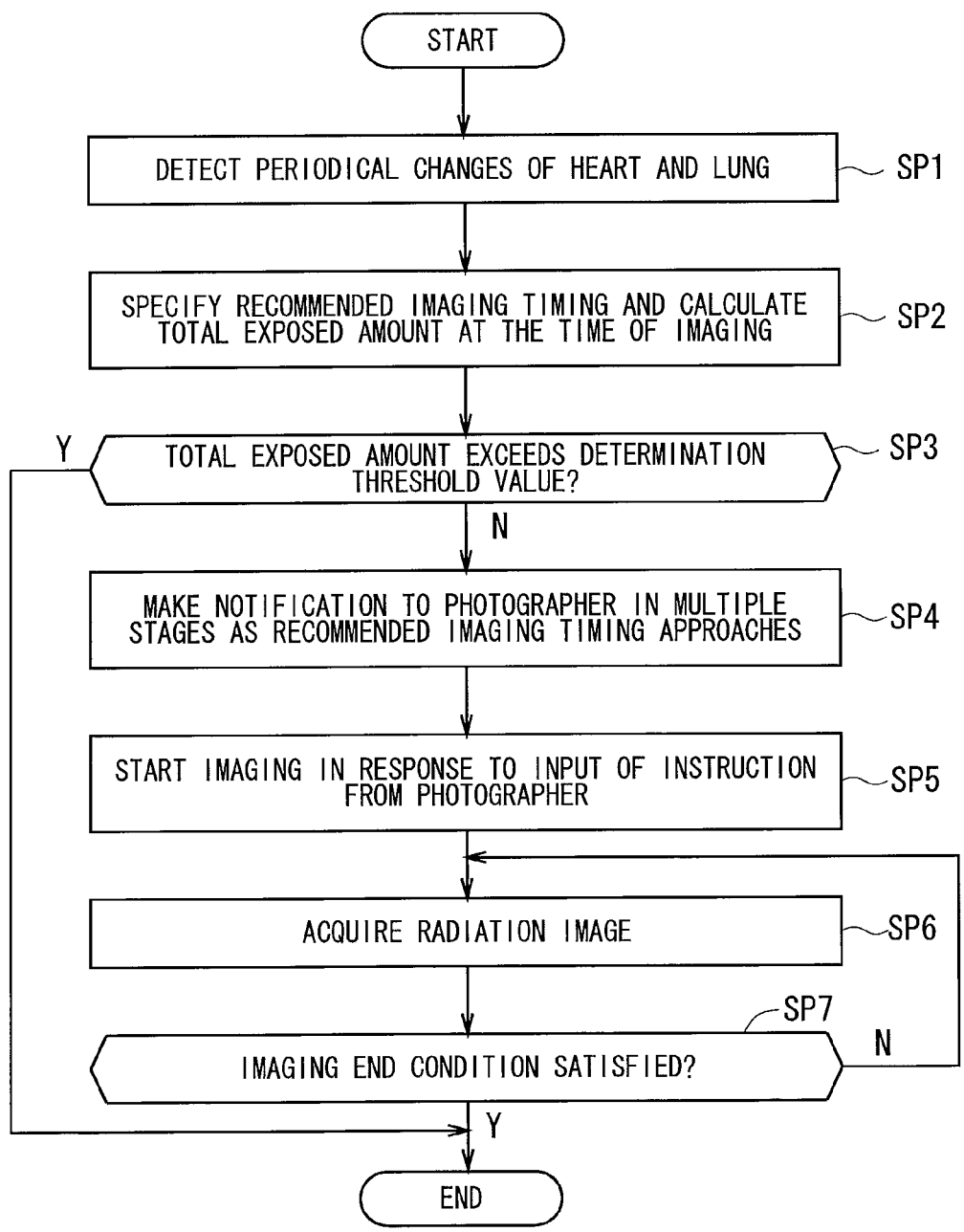
FIG. 14 is a flowchart describing a basic operation realized in the dynamic radiographic imaging system 100B according to the third embodiment.

Next, FIG. 14 is a view showing an operation flow of the dynamic radiographic imaging system 100B according to the third embodiment. Herein, steps SP1, SP2, SP5, SP6, and SP7 are similar to steps ST1, ST2, ST4, ST5, and ST6 of FIG. 12, and hence the description thereof will be omitted.

In the third embodiment, the following steps are added due to the addition of the total exposed amount calculation unit 125B and the forcible ending unit 126, which did not exist in the first embodiment.

In other words, as shown in FIG. 14, if the parameter reflecting the total amount of radiation irradiation after the start of imaging calculated by the total exposed amount calculation unit 125B satisfies a predetermined condition (total exposed amount exceeds determination threshold value) in step SP3, the forcible ending unit 126 forcibly ends the present operation flow, thus cancelling the routine to start the irradiation of radiation on the test subject M. This is preferably character displayed on the display unit 34, so that the photographer is able to know the reason the imaging was forcibly cancelled.

If the total exposed amount does not exceed the determination threshold value, the process proceeds to step SP4, and the notifying section 240 makes the notification to the photographer in multiple stages as the recommended imaging timing approaches by the notification information generated by the notification information generating section 130.

ST5, ST6, and ST7 are performed as steps similar to those in the first and second embodiments, and then the present operation flow is terminated. The display of the total exposed amount in multiple stages by the progress bar CE of FIG. 7 is also used in the present embodiment.

Thus, in the dynamic radiographic imaging system 100B, the imaging necessary and sufficient for diagnosis can be realized even by an unskilled person by forcibly canceling the imaging.

<4. Variant>

The embodiments of the present invention haven been described, but the present invention is not limited to the embodiments described above and various modifications can be made.

The recommended imaging start timing in the embodiments described above is the timing to start the radiation irradiation (imaging) from a state in which the radiation irradiation (imaging) is not being carried out, but may be a timing to start imaging at high irradiation amount if there is an imaging mode at low irradiation amount and an imaging mode at high irradiation amount as in the technique disclosed in Japanese Patent Publication Laid-Open No. 2008-228914. In this case, the heartbeat information and the breathing information are obtained by the analysis of the image obtained in the imaging at low irradiation amount, and then the timing to start the imaging at high irradiation amount (recommended imaging start timing) may be specified.

Even if the notification of the recommended imaging start timing is made, the photographer may not perform the imaging start operation at such timing. In view of such case as well, the notification of the recommended imaging start timing is made not only once, but the notification is preferably repeated each time the phase condition corresponding to the recommended imaging start timing is satisfied. As a matter of course, if the photographer desires to perform the imaging start operation at a timing other than the recommended imaging start timing with a special intention, the notification can be temporarily stopped by providing a cancel button for the notification of the recommended imaging start timing on the operation unit.

If the appropriate recommended imaging start timing differs depending on the type of disease to detect, a plurality of recommended imaging start timing generating conditions may be defined in advance, and the photographer may selective and operate one of the conditions from the operation unit to select the optimum imaging start timing for every disease.

In the present invention, the site where the geometric state time changes periodically in the portion to be imaged of the body is the target of phase detection, but may not be merely heart and lung and may be other organs that perform involuntary motion such as peristalsis, or may be a site that performs voluntary motion such as muscles and joints. In the latter case, the dynamic imaging is carried out while having the test subject repeatedly perform the same operation.

The subject is not merely a human body and may be a body of an animal.

EXPLANATION OF REFERENCE NUMERALS 1 imaging device
2 imaging console
3 diagnosis console
4 electrocardiographic monitor
11 irradiation unit
12 radiation irradiation control device
13 image capturing unit
14 reading control device
21, 21A, 21B control unit
24, 24A display unit
41 phase detecting section
100, 100A, 100B dynamic radiographic imaging system
110 detecting section
120, 120A, 120B recommended imaging timing specifying section
125A, 125B total exposed amount calculation unit
126 forcible ending unit
130 notification information generating section
140 image capturing control section
240 notifying section
241 warning unit
M subject (test subject)

The invention claimed is:

1. A dynamic radiographic imaging system that performs imaging of a radiation image of a subject, said subject being a human body or a body of an animal, the dynamic radiographic imaging system comprising:
a detecting section that detects periodic changes of a predetermined site of said subject;
a recommended imaging start timing specifying section that specifies a recommended imaging start timing based on a detection result of said detecting section;
a notifying section that makes a notification to a photographer in multiple stages as said recommended imaging start timing approaches;
an operation unit that receives an instruction input from said photographer to start radiation imaging of said subject;
an imaging control unit that starts the radiation imaging of said subject in response to the instruction input by said operation unit; and
a second detecting section that detects periodic changes of another site different from said predetermined site of said subject,
wherein said recommended imaging start timing specifying section specifies a timing at which a first specific phase in the periodic changes of said predetermined site and a second specific phase in the periodic changes of said another site overlap as said recommended imaging start timing.

2. The dynamic radiographic imaging system according to claim 1, wherein
said predetermined site is one of heart and lung of said subject; and
said another site is the other one of the heart and the lung of said subject.

* * * * *